United States Patent
Kopczacki et al.

(10) Patent No.: US 9,573,921 B2
(45) Date of Patent: Feb. 21, 2017

(54) SUBSTITUTED N, N-DIMETHYLAMINOALKYL ETHERS OF ISOFLAVANONE OXIMES AS $H_1$-RECEPTOR ANTAGONISTS

(71) Applicant: POLFARMEX S.A., Kutno (PL)

(72) Inventors: Piotr Kopczacki, Kutno (PL); Mieczyslaw Wosko, Kutno (PL); Jaroslaw Walczak, Kutno (PL); Krzysztof Walczynski, Lodz (PL)

(73) Assignee: Polfarmex S.A., Kutno (PL)

( * ) Notice: Subject to any disclaimer, the term of this patent is extended or adjusted under 35 U.S.C. 154(b) by 0 days.

(21) Appl. No.: 15/023,210

(22) PCT Filed: Sep. 30, 2013

(86) PCT No.: PCT/PL2013/000126
§ 371 (c)(1),
(2) Date: Mar. 18, 2016

(87) PCT Pub. No.: WO2015/047113
PCT Pub. Date: Apr. 2, 2015

(65) Prior Publication Data
US 2016/0237055 A1 Aug. 18, 2016

(51) Int. Cl.
| | | |
|---|---|---|
| A61K 31/22 | (2006.01) | |
| C07D 311/58 | (2006.01) | |
| C07D 311/68 | (2006.01) | |
| C07D 407/04 | (2006.01) | |
| C07D 405/04 | (2006.01) | |

(52) U.S. Cl.
CPC .......... *C07D 311/68* (2013.01); *A61K 31/22* (2013.01); *C07D 405/04* (2013.01); *C07D 407/04* (2013.01)

(58) Field of Classification Search
CPC .................................... C07D 311/58
USPC ........................... 514/546; 549/398
See application file for complete search history.

(56) References Cited

U.S. PATENT DOCUMENTS

| | | | | |
|---|---|---|---|---|
| 4,545,993 A * | 10/1985 | Okamoto | ............. | C07D 311/58 514/456 |
| 5,210,234 A * | 5/1993 | Evans | ................. | C07D 311/58 549/398 |
| 6,008,245 A * | 12/1999 | Brendel | ............... | C07D 311/72 514/456 |
| 6,060,506 A * | 5/2000 | Catt | ..................... | C07D 307/79 514/450 |
| 7,259,266 B2 * | 8/2007 | Carter | ................. | C07D 311/58 549/398 |
| 7,812,183 B2 * | 10/2010 | Zhang | ................. | C07D 311/58 549/398 |

FOREIGN PATENT DOCUMENTS

JP  45-27577 B  9/1970

OTHER PUBLICATIONS

Królikowska et al., "Synteza Eterów β-Dwuetyloaminoetylowych Oksymów Flawanonów," [Synthesis of beta-diethylaminoethyl ethers of flavanone oximes] *Acta Poloniae Pharmaceutica* 34(4):445-446, 1977.
Królikowska et al., "Synteza Eterów N,N-Dwuetyloaminoetylowych Oksymów Flawanonów Oraz Badanie Ich Właściwości Przeciwhistaminowych I Spazmolitycznych," [Synthesis of N,N-diethylaminoethyl ethers of flavanone oximes and the study of their antihistaminic and spasmolytic properties] *Acta Poloniae Pharmaceutica* 36(6):667-671, 1979.

* cited by examiner

*Primary Examiner* — Raymond Henley, III
(74) *Attorney, Agent, or Firm* — Seed IP Law Group LLP

(57) ABSTRACT

The present invention relates to compounds of formula (I), and salts thereof and the pharmaceutical composition containing them in treatment of various diseases, as allergic rhinitis where $R_1$ and $R_2$ are, independently, hydrogen, halogen, $C_{1-3}$ alkyl or $C_{1-3}$alkoxy; $R_3$ is phenyl optionally substituted by $R_4$ and $R_5$ which are, independently hydrogen, halogen, $C_{1-3}$ alkyl, C1-3-alkoxy, fluoro-, difluoro- and trifluoromethyl, nitrile group, N,N-di$C_{1-3}$alkyl-amide, carbo$C_{1-3}$ alkoxy or $C_{1-3}$alkylsulphone groups; $R_3$ is pyridyl group containing nitrogen at various positions in the benzene ring, n is one of the integers 1 or 2.

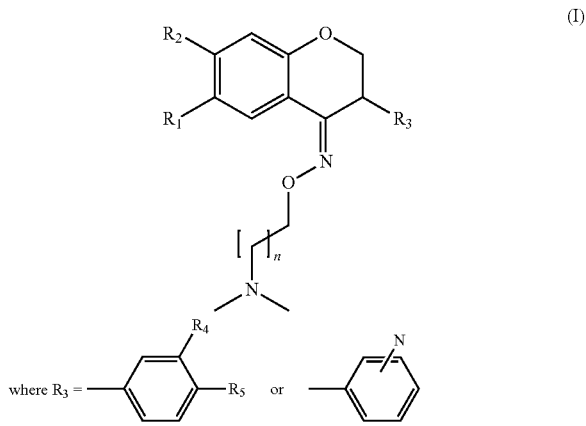

7 Claims, No Drawings

SUBSTITUTED N,N-DIMETHYLAMINOALKYL ETHERS OF ISOFLAVANONE OXIMES AS $H_1$-RECEPTOR ANTAGONISTS

TECHNICAL FIELD

The present invention relates to novel substituted N,N-dimethylaminoalkyl ethers of isoflavanone oximes as $H_1$-receptor antagonists having valuable pharmacological properties, especially against inflammatory diseases and allergic conditions. Compounds of this invention are antagonists of the histamine-$H_1$ receptors.

BACKGROUND ART

Tsujikawa et al., in JP pat. No. 45027577 granted Sep. 9 1970 discloses histamine $H_1$-receptor antagonists which also possess anti-acetlocholine activities of the formula:

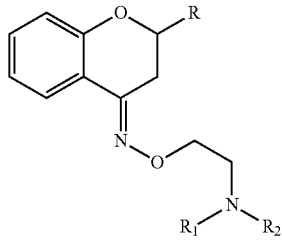

where:
R is phenyl or substituted phenyl; and
$R_1=R_2$ is methyl

Kròlikowska and Perka—Acta Polon. Pharm, XXXIV, No. 4, 445-446, 1977 and Jerzmanowska and Blasiński PL Pat. No. 100895 granted Feb. 15 1979;—is quite similar to disclosure of Tsujikawa et al., although R may also be methyl or disubstituted phenyl and $R_1=R_2$ is ethyl. These compounds are weak antihistaminic agents with spasmolytic properties.

The major structural differences between the compounds of the present invention and those of the said patents and paper is the presence of various substituents at position 3 of N,N-dimethylaminoalkyl ethers of isoflavanone oximes. The compounds disclosed in this invention present an almost exclusive $H_1$ antihistaminic pharmacological activity and are therefore devoid of action on other pharmacological receptors. Because of this selectivity in action, they are valuable instruments in treating allergic-type conditions.

DISCLOSURE OF INVENTION

Technical Problem

Histamine plays a key role in allergy and inflammation. The $H_1$ receptor has been a target for drug discovery for many years, and $H_1$ receptor antagonists have proved to be effective therapeutic agents for the treatment of allergic rhinitis. However, classical antihistamines agents (first-generation class) have several limitations which complicate their clinical use, such as nonselective pharmacological activity and central nervous system (CNS) activity. $H_1$-Antagonists (promethazine, diphenhydramine, cyclazine) demonstrate e.g. muscarine receptor antagonist activity, which may produce anticholinergic side effects. The sedative activity of $H_1$-antagonists is associated with binding to cerebral $H_1$ receptors. The focus of newer $H_1$-antagonists has been an efficacy with diminished sedative liability. These agents (second-generation class—"nonsedating antihistamines") are used in rhinitis, hay fever, asthma and obstructive airway disease. As opposed to classical antihistamine, the more recent $H_1$-antagonists loratadine, astemizole, and temelastine, have poor access to CNS which produces nonsedating antihistaminic activity in the clinic. However since late 1980's, reports began to appear indicating that patients who took intentional overdoses of terfenadine or astemizole could develop a classical form of ventricular arrhythmia, torsades de pointes, which has been previously associated with quinidine and other antiarrhythmic drugs. Many $H_1$-antihistamines have now been examined for their cardiac actions. Astemizole and terfenadine, among the others, belong to group of antihistamines with cardiac effects at their antihistamine concentrations, and from this reason were removed from the market. The newest antihistamine agent, desloratadine, an active metabolite of loratadine has been categorized under the third-generation antihistamine.

Technical Solution

The present invention relates to a compound, including enantiomers, stereoisomers, cis-, trans-isomers and their racemic mixture and mixture of geometric isomers, or pharmaceutically acceptable salts or solvates of said compound, said compound having the general structure shown in formula (I)

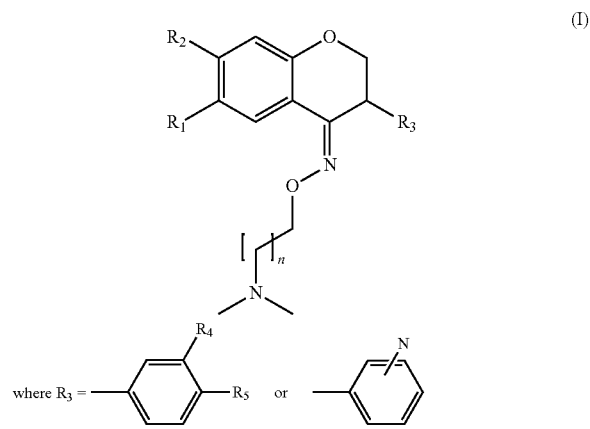

wherein
$R_1$ and $R_2$ are, independently, hydrogen, halogen, $C_{1-3}$alkyl or $C_{1-3}$alkoxy;
$R_3$ is phenyl optionally substituted by $R_4$ and $R_5$ which are, independently hydrogen, halogen, $C_{1-3}$alkyl, $C_{1-3}$alkoxy, fluoro-, difluoro- and trifluoromethyl, nitrile group, N,N-di$C_{1-3}$alkylamide, carbo$C_{1-3}$alkoxy or $C_{1-3}$alkylsulphone groups; $R_3$ is pyridinyl group containing nitrogen at various positions in the benzene ring.
n is one of the integers 1 or 2.

The compound of formula (I) mentioned above where $R_1$ and $R_2$ are $C_{1-3}$alkyl groups, and $R_3$=phenyl, and the optional substituents in $R_4$ and $R_5$ are hydrogen, fluorine, chlorine or bromine.

The compound of formula I mentioned above where $R_1$ and $R_2$ are $C_{1-3}$alkoxy groups and $R_3$=phenyl, and the optional substituents in $R_4$ and $R_5$ are hydrogen, fluorine, chlorine or bromine.

The compound of formula (I) where $R_1$ and $R_2$ are fluorine, chlorine or bromine groups and $R_3$=phenyl, and the optional substituents in $R_4$ and $R_5$ are hydrogen, fluorine, chlorine or bromine.

The compound of formula (I) where $R_1$ and $R_2$ are hydrogen and $R_3$=phenyl, and the optional substituents in $R_4$ are hydrogen or methyl or chlorine and $R_5$ are hydrogen or methyl or fluorine or chlorine or methyl group or methoxy group or nitrile group.

The compound of formula (I) where $R_1$ and $R_2$ are hydrogen, fluorine, chlorine or bromine and $R_3$=unsubstituted pyridynyl, the pyridynyl moiety contains nitrogen at 3-position in benzene ring.

A pharmaceutical composition having histamine $H_1$-antagonists activity comprising a histamine blocking effective amount of a compound according to formula (I) mentioned above and a pharmaceutically acceptable carrier.

The present invention relates to a group of new compounds with N,N-dimethylaminoalkyl ethers of isoflavanone oximes structures having potent selectivity $H_1$ antihistaminic activity.

The compounds subject of the present invention have the following general formula (I):

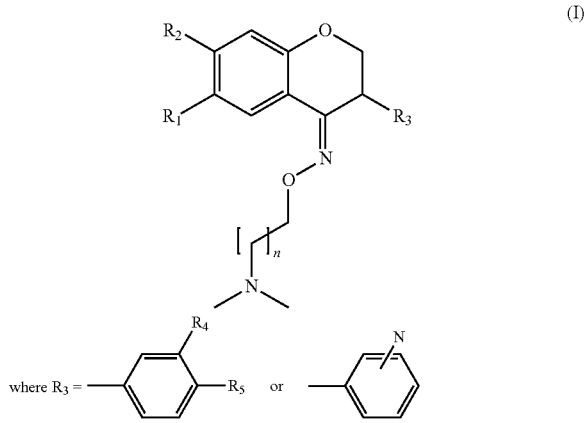

and pharmaceutically acceptable acid addition salts therefore, in which $R_1$ and $R_2$ are, independently, hydrogen, halogen, $C_{1-3}$alkyl or $C_{1-3}$alkoxy;

$R_3$ is phenyl optionally substituted by $R_4$ and $R_5$ which are, independently hydrogen, halogen, $C_{1-3}$alkyl, $C_{1-3}$alkoxy, fluoro-, difluoro- and trifluoromethyl, nitrile group, N,N-di$C_{1-3}$alkyl-amide, carbo$C_{1-3}$alkoxy or $C_{1-3}$alkylsulphone groups; $R_3$ is pyridynyl group containing nitrogen at various positions in the benzene ring.

n is one of the integers 1 or 2;

In the compounds involved in this invention, the halogen substituent is chlorine, bromine or fluorine. The pharmaceutically acceptable salts are derived from such organic and inorganic acids as: acetic, maleic, malonic, fumaric, lactic, citric, tartaric, succinic, oxalic, hydrochloric, hydrobromic, sulfuric, phosphoric, and similarly known acceptable acids.

Examples of alkyl groups for $R_1$ and $R_2$, for $R_3$=phenyl, and the optional substituents in $R_4$ and $R_5$ are hydrogen, fluorine, chlorine or bromine.

Examples of alkoxy groups for $R_1$ and $R_2$, for $R_3$=phenyl, and the optional substituents in $R_4$ and $R_5$ are hydrogen, fluorine, chlorine or bromine.

Examples of halogens for $R_1$ and $R_2$, for $R_3$=phenyl, and the optional substituents in $R_4$ and $R_5$ are hydrogen, fluorine, chlorine or bromine.

Where $R_3$ is phenyl, $R_1$ and $R_2$ can be hydrogen, $C_{1-3}$alkyl, particularly methyl, or halogen, particularly chlorine.

Preferably $R_1$ and $R_2$ are hydrogen.

Preferably n is 1.

Preferably $R_4$ is hydrogen and $R_5$ is halogen.

When $R_3$ is optionally substituted phenyl preferably the phenyl moiety contains a maximum of one substituent.

Examples of optionally substituted phenyl groups for $R_3$ are: phenyl, 3-fluorophenyl, 4-fluorophenyl, 3-chlorophenyl, 4-chlorophenyl, 3-bromophenyl, 4-bromophenyl, 3-methoxyphenyl, 4-methoksyphenyl, 4-trifluorometyhylphenyl, 4-nitrilophenyl, 4-acetamidophenyl, 4-methylsulfonylphenyl, and 4-carbomethoxyphenyl.

When $R_3$ is unsubstituted pyridynyl preferably the pyridynyl moiety contains nitrogen in 3-position in benzene ring.

The compounds of formula (I) exhibit optical and geometrical activity and all isomers in resolved and cis-trans and racemic forms are included within the scope of this invention.

The compounds of formula (I) can be prepared by reacting a compound of formula (II)

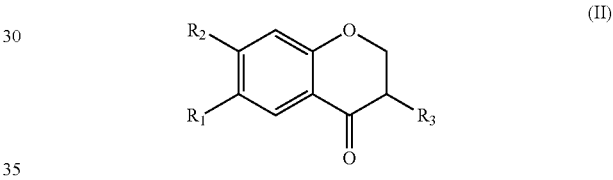

where
$R_1$, $R_2$ and $R_3$ are as defined with reference to formula (I)
with a compound of formula (III)

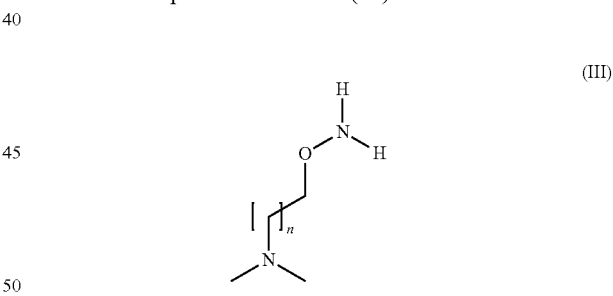

n is one of the integers 1 or 2

This reaction can be carried out in a solvent at an elevated temperature, for example at from 40° C. to 80° C. The choice of solvent is affected by solubility characteristics of the reactants. Preferably the solvent is pyridine, a picoline or mixture of picolines or mixture of pyridine or picolines with and $C_{1-6}$alkanol, preferably ethanol or 1-propanol.

The pharmaceutically acceptable salts of compounds of formula (I) can be prepared by standard methods, for example by reacting a solution of the compound of formula (I) with a solution of the acid.

The compound of formula (II) in which $R_1$=$R_2$=H, and $R_3$ is phenyl or substituted phenyl or disubstitutedphenyl or pyridynyl group containing nitrogen at position 3 or 4 in the benzene ring can be prepared by a three-step synthesis including: palladium-catalyzed cross-coupling reaction of 3-halogenochromones (IV) with the appropriate arylboronic acids (V), to isoflavones, reduction with NaBH₄ in alcohol to isoflavan-4-ols and oxydation of hydroxyl group with pyridinium chlorochromate (PCC) to desired isoflavanones (II) (Hoshino et al. *Bulletin of the Chemical Society of Japan*, 1988, vol. 61, p. 3008-3010). Pyridynyl derivatives of isoflavanones 205 (II) can be directly obtained by hydrogenation of isoflavone with a catalytic amount of palladium on charcoal in acetone (Delcanale et al., EP 1229036 (2002))

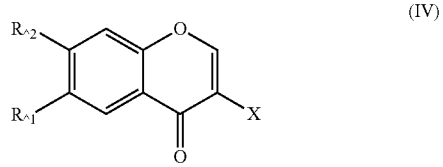

Where X can be chlorine, bromine or iodine
with a compound of formula (V)

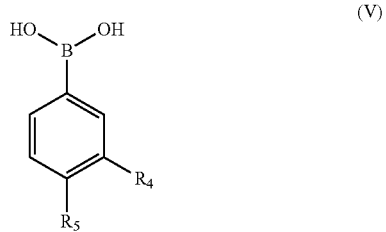

The compound of formula (II) in which $R_1$ and $R_2$ are, independently, halogen, $C_{1-3}$alkyl or $C_{1-3}$alkoxy and $R_3$ is phenyl or substituted phenyl or disubstitutedphenyl or pyridyl group containing nitrogen at position 2 in the benzene ring can be obtained by a two-step synthesis including: cyclization reaction of 1-(2-hydroxy- or 4- or 5-substituted or 4,5-disubstitutedphenyl)-2-pyridin- or 3- or 4- or 3,4 disubstitutedphenyl-2-yl-ethanone (VI) with N,N-dimethylformamide dimethyl acetal (VII), to 3-substituted-4H-chromen-4-ones and hydrogenation with a catalytic amount of palladium on charcoal in acetone yield to desired isoflavanones (Lowe at al, Journal of Heterocyclic Chemistry, 2004, 41(3), 317-326; Oldfield at al. *Tetrahedron*, 2004, 60(8), 1887-1893).

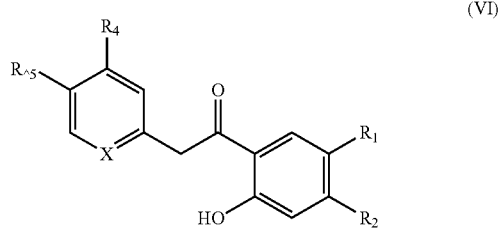

where H═CH or N with a compound of formula (VI)

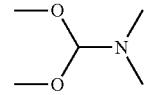

The compounds of formula (III) were obtained by standard methods according to Cerri et al. *J. Med. Chem.*, 2000, 43 (12), pp 2332-2349.

A pharmaceutical composition having histamine $H_1$-antagonists activity comprising a histamine blocking effective amount of a compounds of formula (I).

The following examples illustrate the preparation of representative compounds of this invention.

EXAMPLE 1

Preparation of N,N-dimethyl-2-[[3-(4-methylphenyl)-2,3-dihydrochromen-4-ylidene]-amino]oxy-ethanamine To a solution of 4'-methylisoflavone (0.365 g, 0.00155 mole) in methanol (36.5 mL), sodium borohydride was added in portions over 15 minutes at room temperature. The reaction mixture was stirred for a further 15 minutes and 120 mL water was added. This was extracted with ethyl acetate. The organic layer was dried over anhydrous magnesium sulphate and concentrated to yield 0.37 g of crude 4'-methylisoflavan-4-ol which was used without purification in the next step.

To a solution of the above product (0.37 g) in dichloromethane (9.2 mL), pyridinium chlorochromate (PCC) (0.67 g, 0.0031 mole) and anhydrous sodium acetate (0.141 g, 0.00172 mole) were added. The reaction mixture was stirred at room temperature for 1 h and 250 mL water was added. This was extracted with ethyl acetate. The organic layer was dried over anhydrous magnesium sulphate and concentrated to give the crude 4'-methylisoflavanone which was purified by column chromatography.

$C_{16}H_{14}O_2$, (238.29); yield 81%; mp 86.5-87.0° C., $^1$H NMR (CDCl₃, 300 MHz, ppm): δ 7.95 (d, J=7.8 Hz, 1H, 5-H), 7.49 (t, J=7.8 Hz, 1H, 7-H), 7.15 (m, 4H, Ar—H), 6.99-7.06 (m, 2H, 6-H, 8-H), 4.63 (d, J=6.6 Hz, 2H, 2-H), 3.96 (t, J=6.9 Hz, 1H, 3-H), 2.33 (s, 3H, Ar—CH₃); TLC (hexane:ethyl acetate—9:1), $R_f$ 0.68

To a solution of 4'-methylisoflavanone (0.289 g, 0.0012 mole) in mixture of pyridine (6.12 mL) and dry ethanol (2.45 mL), 2-(dimethylamino)ethoxyamine dihydrochloride (0.433 g, 0.00245 mole) was added. The reaction mixture was stirred at 80° C. for 15 h while being monitored by TLC. After completion, the reaction mixture was poured into water (50 mL) and extracted with ether. The ethereal solution was dried over anhydrous magnesium sulphate. The solvent was evaporated to give the crude N,N-dimethyl-2-[[3-(4-methylphenyl)-2,3-dihydrochromen-4-ylidene]amino]oxyethan-amine as a sticky oil which was purified by column chromatography.

$C_{20}H_{24}N_2O_2$ (324.43); yield 88%; $^1$H NMR (CDCl₃, 300 MHz, ppm): δ 7.98 (dd, 1H, J=7.9, J=1.6, 8-H), 6.86-7.26 (m, 7H, Ar—H), 4.17-4.45 (m, 5H, 2-H, 3-H, OCH₂), 2.42-2.64 (m, 2H, NCH₂), 2.26 (s, 3H, Ar—CH₃), 2.20 (s, 6H, N(CH₃)₂); TLC (hexane:acetone:TEA—70:30:2), $R_f$ 0.47

Elemental analysis for fumaric acid salt $C_{20}H_{24}N_2O_2 \cdot C_4H_4O_4$ (440.50); mp$_{fumaric\ acid\ salt}$ 97-104° C.

|            | C      | H     | N     |
|------------|--------|-------|-------|
| calculated | 65.44% | 6.41% | 6.36% |
| found      | 65.08% | 6.25% | 6.28% |

EXAMPLE 2

Preparation of N,N-dimethyl-2-[[3-(2-pyridinyl)-2,3-dihydrochromen-4-ylidene]-amino]oxyethanamine To a solution of 1-(2-hydroxyphenyl)-2-pyridin-2-yl-ethanone (0.639 g, 0.003 mole) in DMF (12.0 mL), N,N-dimethylformamide dimethyl acetal (0.465 g, 0.0039 mole) was added. The reaction mixture was stirred at room temperature for 6 h. After completion, the reaction mixture was poured into water (100 mL) and extracted with ethyl acetate. The organic layer was dried over anhydrous magnesium sulphate and concentrated to give the crude 3-(2-pyridinyl)-4H-chromen-4-one which was purified by column chromatography.

$C_{14}H_9NO_2$ (223.23); yield 87%; mp 117-118° C.; $^1$H NMR (CDCl$_3$, 300 MHz, ppm): δ 8.85 (s, 1H, 2-H), 8.60 (m, 1H, 6'-H$_{Py}$), 8.42 (d, J=8.1 Hz, 1H, 5-H), 8.32 (d, J=8.1 Hz, 1H, 4'-H$_{Py}$), 7.64-7.78 (m, 2H, 7-H and 8-H), 7.40-7.51 (m, 2H, 6-H and 3'-H$_{Py}$), 7.22-7.29 (m, 1H, 5'-H$_{Py}$); TLC (hexane:acetone—75:25), R$_f$ 0.57

3-(2-pyridinyl)-4H-chromen-4-one (0.23 g, 0.001 mole) in acetone (15 mL), palladium on carbon (Pd/C 10%, 0.1 g) was added. Subsequently, hydrogen atmosphere was applied, and after 4 h of stirring at room temperature, the next portion of Pd/C 10%, (0.1 g) was added and the resulting suspension was stirred for another 2 h. The progress of the reaction was monitored by TLC. The suspension was filtered, the filtrate was evaporated and the residue was purified by column chromatography.

$C_{16}H_{16}NO_2$ (225.25); yield 40%; mp 119° C.; $^1$H NMR (CDCl$_3$, 300 MHz, ppm): δ 8.56 (s, 1H, 6'-H$_{Py}$), 7.97 (dd, 1H, J=7.9, J=1.7, 5-H), 7.69 (td, J=7.9 Hz, J=1.7, 1H, 4'-H$_{Py}$), 7.50-7.56 (m, 1H, 6-H), 7.44 (d, J=7.9, 1H, 7-H), 7.24-7.28 (m, 1H, 8-H), 7.00-7.11 (m, 2H, 3'-H$_{Py}$ and 5'-H$_{Py}$), 5.34 (br s, 1H, 3-H), 4.81 (d, J=11.5, 1H, 2-H), 4.53 (d, J=11.5, 1H, 2-H); TLC (hexane:acetone—75:25), R$_f$ 0.37

To a solution of 3-(2-pyridinyl)-2,3-dihydro-4H-chromen-4-one (0.0097 g, 0.00043 mole) in mixture of pyridine (2.15 mL) and dry ethanol (0.86 mL), 2-(dimethylamino)ethoxyamine dihydrochloride (0.0015 g, 0.00086 mole) was added. The reaction mixture was stirred at 80° C. for 12 h while being monitored by TLC. After completion, the reaction mixture was poured into water (50 mL) and extracted with ethyl acetate. The organic layer was dried over anhydrous magnesium sulphate. The solvent was evaporated to give the crude N,N-dimethyl-2-[[3-(2-pyridinyl)-2,3-dihydrochromen-4-ylidene]amino]oxyethanamine as a sticky oil which was purified by column chromatography.

$C_{20}H_{24}N_2O_2$ (324.43); yield 88%; $^1$H NMR (CDCl$_3$, 300 MHz, ppm): δ 8.51 (d, 1H, J=4.8, 6'-H$_{Py}$), 7.99 (d, 1H, j=7.7, 8-H), 7.67-7.77 (m, 2H, 4'-H$_{Py}$ and 7-H), 7.26-7.34 (m, 1H, 6-H), 7.12-7.16 (m, 1H, 5-H), 6.98-7.03 (m, 2H, 3'-H$_{Py}$ and 5'-H$_{Py}$), 4.05-4.18 (m, 4H, 2-H, OCH$_2$), 3.83-3.91 (m, 1H, 3-H), 2.73-2.83 (m, 1H, NCH$_2$ isomer Z), 2.22 (s, 6H, N(CH$_3$)$_2$), 1.99-2.05 (m, 1H, NCH$_2$ isomer E); TLC (hexane:acetone:TEA—70:30:2), R$_f$ 0.36 Elemental analysis for difumaric acid salt $C_{18}H_{21}N_3O_2 \cdot 2C_4H_4O_4$ (543.54); mp$_{difumaric\ acid\ salt}$=193-195° C.

|            | C      | H     | N     |
|------------|--------|-------|-------|
| calculated | 57.46% | 5.38% | 7.73% |
| found      | 57.61% | 5.18% | 7.86% |

All obtained final free bases were treated with methanolic fumaric acid and fumaric acid salts were precipitated with dry diethyl ether and crystallized twice from ethanol.

The compounds of this invention were established to be histamine. H$_1$-antagonists by subjecting them to the following standard test procedures for H$_1$-blocking activity:

Male guinea pigs weighing 300-400 g were sacrificed by a blow on the head. The ileum was excised and placed in phosphate buffer at room temperature (pH 7.4) containing (mM) NaCl (136.9); KCl (2.68); NaHPO$_4$ (7.19). After flushing the intraluminal contents, segments of about 2 cm long were cut and mounted for isotonic contractions in water jacked 20 mL organ baths filled with oxygenated (O$_2$: CO$_2$=95:5, v/v) Krebs buffer containing (mM) NaCl (117.5); KCl (5.6); MgSO$_4$ (1.18); CaCl$_2$ (2.5); NaH$_2$PO$_4$ (1.28); NaHCO$_3$ (25); glucose (5.5) and indomethacin (1.10$^{-6}$ mol/L) at 37° C. under a constant load of 0.5 g. After a 30 min equilibration period with washings every 10 mins, a sub maximal priming dose of histamine (1 μM) was given and washed out (standard washing procedure: 3 changes of buffer during 30 mins). After washing out, the antagonistic activity of given compounds was measured by recording a Concentration Response Curve (CRC) for histamine in the presence of the testing compounds which was added 10 mins before histamine. This procedure was repeated with higher concentrations of the compounds. The antagonism was of a competitive nature causing a parallel shift of the CRC. The pA$_2$-values were calculated according to O. Arunlakshana, H. O. Schild, Br. *J. Pharmacol.* 1959, 14, 48-58. The pA$_2$ values were compared with the potency of pyrilamine.

Selected compounds were tested for H$_3$ antagonistic effects in vitro, following standard methods, using the guinea pig ileum (R. C. Vollinga, O. P. Zuiderveld, H. Scheerens, A. Bast, H. Timmerman, *Meth. Find. Exp. Cli. Pharmacol.* 1992, 105, 747-751). Male guinea pigs weighing 300-400 g were sacrificed by a blow on the head. A portion of the small intestine, 20-50 cm proximal to the ileocaecal valve (jejunum), was removed and placed in Krebs buffer (composition (mM) NaCl 118; KCl 5.6; MgSO$_4$ 1.18; CaCl$_2$ 2.5; NaH$_2$PO$_4$ 1.28; NaHCO$_3$ 25; glucose 5.5 and indomethacin (1 10$^{-6}$ mol/L)). Whole jejunum segments (2 cm) were prepared and mounted between two platinum electrodes (4 mm apart) in 20 mL Krebs buffer, continuously gassed with 95% O$_2$:5% CO$_2$ and maintained at 37° C. Contractions were recorded isotonically under 1.0 g tension with Hugo Sachs Hebel-Messvorsatz (T1-2)/HF-modem (Hugo Sachs Electronik, Hugstetten, Germany) connected to a pen recorder. After equilibration for one hour with washings every 10 min, the muscle segments were stimulated maximally between 15 and 20 Volt and continuously at a frequency of 0.1 Hz and a duration of 0.5 msec, with rectangular-wave electrical pulses, delivered by a Grass Stimulator S-88 (Grass Instruments Co., Quincy, USA). After 30 min of stimulation, five minutes before adding (R)-α-methylhistamine, pyrilamine (1.10$^{-5}$ mol/L concentration in organ bath) was added, and then cumulative concentration-response curves (half-log increments) of (R)-α-methylhistamine, H$_3$-agonist, were recorded until no further change in response was found. Five minutes before adding the tested compounds, the pyrilamine (1 10$^{-5}$ mol/L concentration in organ bath) was added, and after 20 minutes cumulative concentration-response curves (half-log increments) of (R)-α-methylhistamine, $H_3$-agonist, were recorded until no further change in response was found. Statistical analysis was carried out with the Students' t-test. In all test p<0.05 was considered statistically significant. The potency of an antagonist is expressed by its $pA_2$ value, calculated from the Schild regression analysis where at least three concentrations were used. The $pA_2$ values were compared with the potency of thioperamide. No one shows any $H_3$-antagonistic activity ($pA_2<4$; for thioperamide $pA_2=8.67$).

INDUSTRIAL APLICABILITY

The pharmacological results obtained characterize the compounds of this invention as $H_1$-receptor antagonists useful in the treatment of mammals experiencing conditions such as asthma, hay fever, allergic rhinitis, atopic dermatitis, conjunctivitis, pruritis, and eczema, or other responses where histamine is released and acts on $H_1$ receptors. As such, they may be administered topically or systemically. Topical administration is advantageously achieved with creams, ointments or lotion, or via aerosol introduction into the respiratory tract. Systematic administration may be orally, nasally, intrabronchially, parenterally or rectally. In each instance, conventional formulation amenable to use in desired administration route is appropriate. Hence, tablets and capsules may be prepared for oral administration, suppositories for rectal administration, isotonic aqueous solutions for intravenous, subcutaneous of intramuscular injection and in aerosol suspensions for inhalation.

As is conventional in the use of anthistamine agents, the appropriate dosage is determined on a subjective basis for initial administration in small amounts, c.a. 0.5-15 mg, followed by increasing quantities up to about 400 mg., depending upon the desired route of administration, until the desired symptomatic relief is obtained. The dosage is personalized in this manner for each patient, based upon size, age, type of discomfort, degree of disability, etc., by the physician.

What is claimed is:

1. A compound, including enantiomers, stereoisomers, cis-, trans-isomers and their racemic mixture and mixture of geometric isomers, or pharmaceutically acceptable salts or solvates of said compound, said compound having the general structure shown in formula (I)

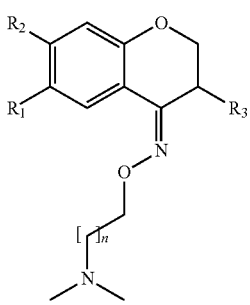
(I)

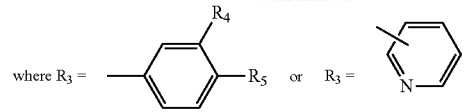

wherein
$R_1$ and $R_2$ are, independently, hydrogen, halogen, $C_{1-3}$alkyl or $C_{1-3}$alkoxy;
$R_3$ is optionally substituted phenyl represented by

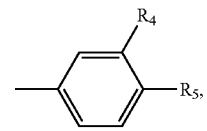

wherein
$R_4$ and $R_5$ are, independently, hydrogen, halogen, $C_{1-3}$alkyl, $C_{1-3}$alkoxy, fluoro-,difluoro- and trifluoromethyl, nitrile group, N,N-di$C_{1-3}$alkylamide, carbo$C_{1-3}$alkoxy or $C_{1-3}$alkylsulphone groups; or
$R_3$ is pyridinyl represented by

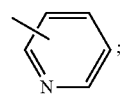

and
n is one of the intergers 1 or 2.

2. The compound of claim 1 where $R_1$ and $R_2$ are $C_{1-3}$alkyl groups, and $R_3$ is optionally substituted phenyl, wherein $R_4$ and $R_5$ are hydrogen, fluorine, chlorine or bromine.

3. The compound of claim 1 where $R_1$ and $R_2$ are $C_{1-3}$alkoxy groups and $R_3$ is optionally substituted phenyl, wherein $R_4$ and $R_5$ are hydrogen, fluorine, chlorine or bromine.

4. The compound of claim 1 where $R_1$ and $R_2$ are fluorine, chlorine or bromine groups and $R_3$ is optionally substituted phenyl, wherein $R_4$ and $R_5$ are hydrogen, fluorine, chlorine or bromine.

5. The compound of claim 1 where $R_1$ and $R_2$ are hydrogen and $R_3$ is optionally substituted phenyl, wherein $R_4$ is hydrogen, methyl or chlorine; and $R_5$ is hydrogen, methyl, fluorine, chlorine methoxy group, or nitrile group.

6. The compound of claim 1 where $R_1$ and $R_2$ are hydrogen, fluorine, chlorine or bromine and $R_3$ is 3-pyridinyl.

7. A pharmaceutical composition having histamine $H_1$-antagonists activity comprising a histamine blocking effective amount of a compound according to claim 1 and a pharmaceutically acceptable carrier.

* * * * *

UNITED STATES PATENT AND TRADEMARK OFFICE
CERTIFICATE OF CORRECTION

PATENT NO. : 9,573,921 B2
APPLICATION NO. : 15/023210
DATED : February 21, 2017
INVENTOR(S) : Piotr Kopczacki et al.

It is certified that error appears in the above-identified patent and that said Letters Patent is hereby corrected as shown below:

Item (72):
"Piotr Kopczacki, Kutno (PL); Mieczyslaw Wosko, Kutno (PL); Jaroslaw Walczak, Kutno (PL); Krzysztof Walczynski, Lodz (PL)"
Should read:
--Piotr Kopczacki, Kutno (PL); Mieczyslaw Wosko, Kutno (PL); Jaroslaw Walczak, Kutno (PL); Krzysztof Walczynski, Kutno (PL)--.

Item (56):
"Królikowska et al., "Synteza Eterów N,N-Dwuetyloaminoetylowych Oksymów Flawanonów Oraz Badanie Ich Wł aściwości Przeciwhistaminowych I Spazmolitycznych," [Synthesis of N,N-diethylaminoethyl ethers of flavanone oximes and the study of their antihistaminic and spasmolytic properties] *Acta Poloniae Pharmaceutica* 36(6):667-671, 1979."
Should read:
--Królikowska et al., "Synteza Eterów N,N-Dwuetyloaminoetylowych Oksymów Flawanonów Oraz Badanie Ich Właściwości Przeciwhistaminowych I Spazmolitycznych," [Synthesis of N,N-diethylaminoethyl ethers of flavanone oximes and the study of their antihistaminic and spasmolytic properties] *Acta Poloniae Pharmaceutica* 36(6):667-671, 1979.--.

Signed and Sealed this
Fourteenth Day of November, 2017

Joseph Matal
*Performing the Functions and Duties of the*
*Under Secretary of Commerce for Intellectual Property and*
*Director of the United States Patent and Trademark Office*